US007105561B2

(12) United States Patent
Carson et al.

(10) Patent No.: US 7,105,561 B2
(45) Date of Patent: Sep. 12, 2006

(54) USE OF ETODOLAC FOR THE TREATMENT OF PROSTATE CANCER

(75) Inventors: Dennis A. Carson, Del Mar, CA (US); Howard B. Cottam, Escondido, CA (US); Souchi Adachi, La Jolla, CA (US); Lorenzo M. Leoni, San Diego, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 10/236,221

(22) Filed: Sep. 5, 2002

(65) Prior Publication Data

US 2003/0078293 A1 Apr. 24, 2003

Related U.S. Application Data

(63) Continuation of application No. 09/360,020, filed on Jul. 23, 1999, now Pat. No. 6,545,034.

(51) Int. Cl.
*A61K 31/40* (2006.01)
(52) U.S. Cl. ..................... 514/411; 514/908
(58) Field of Classification Search ............... 514/411, 514/922
See application file for complete search history.

(56) References Cited

U.S. PATENT DOCUMENTS

| 3,053,255 A | 9/1962 | Meyer |
| 3,710,795 A | 1/1973 | Higuchi et al. |
| 3,843,480 A | 10/1974 | Dreher |
| 3,843,681 A | 10/1974 | Demerson et al. .. 260/326.14 R |
| 3,939,178 A | 2/1976 | Demerson et al. |
| 3,948,254 A | 4/1976 | Zaffaroni |
| 3,948,262 A | 4/1976 | Zaffaroni |
| 3,974,179 A | 8/1976 | Demerson et al. |
| 3,993,073 A | 11/1976 | Zaffaroni |
| 4,041,169 A | 8/1977 | Demerson et al. |
| 4,179,503 A | 12/1979 | Asselin et al. |
| 4,310,509 A | 1/1982 | Berglund et al. |
| 4,337,760 A | 7/1982 | Rubin ....................... 128/1 R |
| 4,460,562 A | 7/1984 | Keith et al. |
| 4,466,953 A | 8/1984 | Keith et al. |
| 4,482,534 A | 11/1984 | Blank |
| 4,485,097 A | 11/1984 | Bell |
| 4,505,891 A | 3/1985 | Ito |
| 4,533,540 A | 8/1985 | Blank |
| 4,542,012 A | 9/1985 | Dell |
| 4,542,013 A | 9/1985 | Keith et al. |
| 4,560,555 A | 12/1985 | Snider |
| 4,585,877 A | 4/1986 | Demerson et al. |
| 4,597,961 A | 7/1986 | Etscorn |
| 4,608,249 A | 8/1986 | Otsuka et al. |
| 4,686,213 A | 8/1987 | Ferdinandi et al. |
| 4,748,252 A | 5/1988 | Ferdinandi et al. |
| 4,806,356 A | 2/1989 | Shaw |
| 4,940,587 A | 7/1990 | Jenkins et al. |
| 5,561,151 A | 10/1996 | Young et al. ................ 514/411 |
| 5,599,946 A | 2/1997 | Vincenzo et al. |
| 5,776,967 A | 7/1998 | Kreft et al. |
| 5,780,435 A * | 7/1998 | Garnick et al. ................ 514/15 |
| 5,811,558 A | 9/1998 | Adger et al. ................ 548/427 |
| 5,824,699 A | 10/1998 | Kreft et al. |
| 5,939,455 A | 8/1999 | Rephaeli |
| 5,955,504 A | 9/1999 | Wechter et al. .............. 514/568 |
| 5,968,974 A | 10/1999 | Kargman et al. |
| 5,981,592 A | 11/1999 | Wechter et al. |
| 6,110,955 A | 8/2000 | Nudelman et al. |
| 6,160,018 A | 12/2000 | Wechter et al. |
| 6,300,313 B1 * | 10/2001 | Engel et al. ................... 514/15 |
| 6,545,034 B1 | 4/2003 | Carson et al. |
| 6,552,055 B1 | 4/2003 | Spiegelman et al. |
| 2002/0042375 A1 | 4/2002 | Heimbrook et al. |
| 2003/0004142 A1 | 1/2003 | Prior et al. |
| 2003/0004143 A1 | 1/2003 | Prior et al. |
| 2005/0239752 A1 | 10/2005 | Carson et al. |

FOREIGN PATENT DOCUMENTS

| CA | 1299577 | 4/1992 |
| DE | 2226340 | 3/1973 |
| EP | 0289262 | 11/1986 |
| GB | 1436893 | 5/1976 |
| WO | WO-96/28148 | 9/1996 |
| WO | WO-97/48391 A3 | 12/1997 |
| WO | WO-98/09603 | 3/1998 |
| WO | WO-98/18490 | 5/1998 |
| WO | WO-98/40078 A1 | 9/1998 |
| WO | WO-00/02555 | 1/2000 |
| WO | WO-00/13410 | 3/2000 |
| WO | WO-01/06990 A2 | 2/2001 |
| WO | WO-02/02125 A1 | 1/2002 |
| WO | WO-02/12188 A2 | 2/2002 |

OTHER PUBLICATIONS

Mycek et al, "Lippincott's Illustrated Reviews, Pharmacology, Second Edition", Lippincott-Raven Publishers, pp. 373 and 387-395 (1997).*
Chemical Abstracts 136:303669, "Induction of apoptosis by cyclooxygenase-2 inhibitors in prostate cancer cell lines", Kamijo et al (2001).*
*The Merck Index, Eleventh Edition,* Budavari, S., et al., (eds.), Merck & Co., Inc., Rahway, N.J., Entry No. 3831—"Etodolac",(1989),p. 608.
In: *Remington's Pharmaceutical Sciences, Eighteenth Edition,* Gennaro, A.R., (ed.), Mack Publishing Company, Easton, PA,(1990),pp. 1115-1121.

(Continued)

*Primary Examiner*—Frederick Krass
(74) *Attorney, Agent, or Firm*—Schwegman, Lundberg, Woessner & Kluth P.A.

(57) ABSTRACT

A method of treating cancer is provided comprising administering an amount of etodolac to a subject afflicted with cancer that is effective to reduce the viability and/or to sensitize the cancer to an anti-cancer agent.

8 Claims, 9 Drawing Sheets

OTHER PUBLICATIONS

Abramson, S..B. ,et al. ,"The Mechanisms of Action of Nonsteroidal Antiinflamatory Drugs", *Arthritis & Rheumatism*, 32 (1), (Jan. 1989),pp. 1-9.

Alexanian, R.. ,et al. ,"The Treatment of Multiple Myeloma", *The New England Journal of Medicine*, 330 (7), (Feb. 17, 1994),pp. 484-489.

Barlogie, B.,et al. ,"Prognostic Factors with High-Dose Melphalan for Refractory Multiple Myeloma.", *Blood*, 72, (1988),2015-2019.

Bataille, R.,et al. ,"Multiple Myeloma", *New England Journal of Medicine*, 336, (1997),1657-1664.

Becker-Scharfenkamp, U..,et al. ,"Evaluation of the Stereoselective Metabolism of the Chiral Analgesic Drug Etodolac by High-Performance Liquid Chromatography", *Journal of Chromatography*, 621 (2), (Nov. 24, 1993),pp. 199-207.

Bellosillo, B..,et al. ,"Aspirin and Salicylate Induce Apoptosis and Activation of Caspases in B-Cell Chronic Lymphocytic Leukemia Cells", *Blood*, 92 (4), (Aug. 15, 1998),pp. 1406-1414.

Berendes, U..,et al. ,"Simultaneous Determination of the Phase II Metabolites of the Non Steriodal Anti-inflammatory Drug Etodolac in Human Urine", *Enantiomer*, 1, Abstract Only, Chemical Abstracts, Abstract No. 126:207064q,(1996),415-422.

Brenna, E..,et al. ,"New Enzymatic and Chemical Approaches to Enantiopure Etodolac", *Tetrahedron*, 53, (1997), 17769-17780.

Brocks, D..R. ,et al. ,"Etodolac Clinical Pharmacokinetics", *Clinical Pharmacokinetics*, 26 (4), (1994),pp. 259-274.

Carson, D..A. ,et al. ,"Oral Antilymphocyte Activity and Induction of Apoptosis by 2-chloro-2'-arabino-fluoro-2'-deoxyadenosine", *Proc. Natl. Acad. Sci. USA*, 89 (7), (Apr. 1992),pp. 2970-2974.

Chinetti, G..,et al. ,"Activation of Proliferator-activated Receptors alpha and Y Induces Apoptosis of Human Monocyte-derived Macrophages", *The Journal of Biological Chemistry*, 273 (40), (Oct. 2, 1998),pp. 25573-25580.

Cunningham, D.,et al. ,"High-dose Melphalan for Multiple Myeloma: Long-term Follow-up Data", *Journal of Clinical Oncology*, 12, (1994),764-768.

Demerson, C..A. ,et al. ,"Etodolic Acid and Related Compounds. Chemistry and Antiinflammatory Actions of Some Potent Di- and Trisubstituted 1,3,4,9-Tetrahydropyrano[3,4-b]indole-1-acetic Acids", *Journal of Medicinal Chemistry*, 19 (3), (1976),pp. 391-395.

Demerson, C..A. ,et al. ,"Resolution of Etodolac and Antiinflammatory and Prostaglandin Synthetase Inhibiting Properties of the Enantiomers", *J. Med. Chem.*, 26 (12), (Dec. 1983),pp. 1778-1780.

Drachenberg, D..F. ,et al. ,"Treatment of Prostate Cancer: Watchful Waiting, Radical Prostatectomy, and Cryoablation", *Seminars in Surgical Oncology*, 18 (1), (Jan./Feb. 2000),pp. 37-44.

Duffy, C..P. ,et al. ,"Enhancement of Chemotherapeutic Drug Toxicity to Human Tumour Cells In Vitro by a Subset of Non-Steroidal Anti-Inflammatory Drugs (NSAIDs)", *European Journal of Cancer*, 34 (8), (Jul. 1998),pp. 1250-1259.

Hahnfeld, L..E. ,et al. ,"Prostate Cancer", *The Medical Clinics of North America—The Aging Male Patient*, 83 (5), (Sep. 1999),pp. 1231-1245.

Harousseau, J..L. ,et al. ,"Double-Intensive Therapy in High-Risk Multiple Myeloma", *Blood*, 79 (11), (Jun. 1, 1992),pp. 2827-2833.

Krajewski, S..,et al. ,"Detection of Multiple Antigens on Western Blots", *Analytical Biochemistry*, 236 (2), Article No. 0160,(May 1996),pp. 221-228.

Landis, S..H. ,et al. ,"Cancer Statistics, 1998", *CA Cancer J. Clin.*, 48 (1), (1998),pp. 6-29.

Lee, D..H. ,"Proteasome Inhibitors: Valuable New Tools For Cell Biologists", *Trends in Cell Biology*, 8, (Oct. 1998),pp. 397-403.

Lehmann, J..M. ,et al. ,"Peroxisome Proliferator-activated Receptors alpha and Y Are Activated by Indomethacin and Other Nonsteroidal Anti-inflammatory Drugs", *The Journal of Biological Chemistry*, 272 (6), (Feb. 7, 1997),pp. 3406-3410.

Leoni, L..M. ,et al. ,"Induction of an Apoptotic Program in Cell-Free Extracts by 2-Chloro-2'-deoxyadenosine 5'-triphosphate and Cytochrome C", *PNAS, USA*, 95 (16), (Aug. 4, 1998),pp. 9567-9571.

Lochmuller, C..H. ,et al. ,"Chromatographic Resolution of Enantiomers—Selective Review", *Journal of Chromatography*, 113 (3), (Oct. 22, 1975),pp. 283-302.

Martel, R..R. ,et al. ,"Anti-inflammatory and Analgesic Properties of Etodolic Acid in Rats", *Canadian Journal of Physiology and Pharrmacology*, 54 (3), (Jun. 1976),pp. 245-248.

Mooney, P..T. ,et al. ,"Cell Pathways' Exisulind 'Aptosyn' Demonstrates Potential to Delay Hormonoe Therapy in Post-Prostatectomy Men at Risk of Prostate Cancer Recurrence", http://biz.yahoo.com/bw/000501/ga_cell_pa_1.html, (May 2000),3 p.

Nardella, Francis.A. ,et al. ,"Enhanced Clearance of Leukemic Lymphocytes in B Cell Chronic Lymphocytic Leukemia (CLL) with Etodolac", *Arthritis & Rheumatism*, 42 (9) Supplement, Abstract No. 41, (Sep. 1999),p. S56.

Ricote, M..,et al. ,"The Peroxisome Proliferator-Activated Receptor-Y is a Negative Regulator of Macrophage Activation", *Nature*, 391, (Jan. 1, 1998),pp. 79-82.

Riedel, D..A. ,et al. ,"The Epidemiology of Multiple Myeloma", *Hematology/Oncology Clinics of North America, Multiple Myeloma*, 6 (2), (Apr. 1992),pp. 225-247.

Royall, J..A. ,et al. ,"Evaluation of 2',7'-Dichlorofluorescin and Dihydrorhodamine 123 as Fluorescnet Probes for Intracellular H2O2 in Cultured Endothelial Cells", *Archives of Biochemistry and Biophysics*, 302 (2), (May 1, 1993),pp. 348-355.

Shiff, S..J. ,et al. ,"Nonsteroidal Antiinflammatory Drugs Inhibit the Proliferation of Colon Adenocarcinoma Cells: Effects on Cell Cycle and Apoptosis", *Experimental Cell Research*, 222, Article No. 0023,(1996),pp. 179-188.

Tang, D..G. ,et al. ,"Target to Apoptosis: A Hopeful Weapon for Prostate Cancer", *The Prostate*, (1997),pp. 284-293.

Van Breemen, R..B. ,et al. ,"Characterization of Oxygen-Linked Glucuronides by Laser Desorption Mass Spectrometry", *Biomed. Mass Spectrom.*, 11, Abstract Only, Chemical Abstracts, Abstract No. 101:106777c,(1984),278-283.

Venuti, M..C. ,et al. ,"Synthesis and Biological Evaluation of omega-(N,N,N-trialkylammonium)alkyl Esters and Thioesters of Carboxylic Acid Nonsteroidal Antiinflammatory Agents", *Pharm. Res.*, 6, Abstract Only, Chemical Abstracts, Abstract No. 112:111681y,(1989),867-873.

Wang, X..,et al. ,"Antipoptotic Action of 1,25-Dihydroxyvitamin D3 Is Associated with Increased Mitochondrial MCL-1 and RAF-1 Proteins and Reduced Release of Cytochrome c", *Experimental Cell Research*, 235 (1), Article No. EX973667,(1997),pp. 210-217.

Wechter, W..J. ,et al. ,"E-7869 (R-Flurbiprofen) Inhibits Progression of Prostate Cancer in the TRAMP Mouse", *Cancer Research*, 60, (Apr. 15, 2000),pp. 2203-2208.

Weiss, H..A. ,et al. ,"Aspirin, Non-Steroidal Anti-Inflammatory Drugs and Protection from Colorectal Cancer: a Review of the Epidemiological Evidence", *Scandinavian Journal of Gastroenterology*, 31 (Suppl. 220), (1996),pp. 137-141.

Wilen, S..H. ,et al. ,"Strategies In Optical Resolutions", *Tetrahedron*, 33 (21), Tetrahedron Report No. 38,(1977),pp. 2725-2736.

*Drug Facts and Comparisons, 1995 Edition*, Wolters Kluwer Co.,(1995),2775-2789.

"1991 New Drugs", *US Pharmacist*, 61, (Sep. 1991),35-40, 42, 44,46, 48-50, 52, 57-58, 60, 62, 64 (Pages not cited are advertisements).

"International Search Report for PCT Application No. PCT/US2004/032185" , (Apr. 20, 2005), 11 pgs.

Brenna, Elisabetta, et al., "New Enzymatic and Chemical Approaches to Enantiopure Etodolac", *Tetrahedron*, vol. 53, No. 52, (1997), 17769-17780.

Heath, Clark W., "Nonsteroidal Antiinflammatory Drugs and Human Cancer", *American Cancer Society*,74(10), (Nov. 15, 1994), 2885-2886.

Kolluri, S. K., et al., "The R-enantiomer of the Nonsteroidal Antiinflammatory Drug Etodolac Binds Retinoid X Receptor and Induces Tumor-Selective Apoptosis", *Proc. Natl. Acad. Sci. USA*, 102(7) (2005), 2525-2530.

Leman, Eddy S., et al., "Characterization of the Nuclear Matrix Proteins in a Transgenic Mouse Model for Prostate Cancer", *Journal of Cellular Biochemistry*, 86, (2002), 203-212.

McCracken, John D.., "Antiproliferative Effects of the Enantiomers of Flurbiprofen", *Journal of Clinical Pharmacology*, 36, (1996), 540-545.

Piazza, Gary A., "Apoptois Primarily Accounts for the Growth-inhibitory Properties of Sulindac Metabolites and Involves a Mechanism That is Independent of Cyclooxygebase Inhibition, Cell Cycles Arrest, and p53 Induction", *Cancer Research*, 57, (Jun. 15, 1997), 2452-2459.

Riley, et al., "New Drugs: a Six Month Review", *US Pharamacist*, 16, (Sep. 1991), 35-64.

Thun, Michael J., "Aspirin, NSAIDs, and Digestive Tract Cancers", *Cancer and Metastasis Reviews 13*, Kluwer Academic Publishers., (1994), 269-277.

Wechter, William J., "R-Flurbiprofen (E-7869), a Chemopreventive and Treatment of Cancer", *Inflammopharmacology*, 8(2), (2000), 189-206.

Wechter, William J., "R-Flurbiprofen Chemoprevention and Treatment of Intestinal Adenomas in the APC$^{Min}$/+Mouse Model: Implications for Prophylaxis and Treartment of Colon Cancer", *Cancer Research*, vol. 57, No. 19, (Oct. 1, 1997), 4316-4324.

Wechter, William J., "Rac-Flurbiprofen Is More Ulcerogenic Than Its (S)-Enantiomer", *Chirality*, vol. 5, No. 7, (1993), 492-494.

\* cited by examiner

USE OF ETODOLAC FOR THE TREATMENT OF PROSTATE CANCER

CROSS-REFERENCE TO RELATED APPLICATION

This application is a continuation of U.S. patent application Ser. No. 09/360,020 filed Jul. 23, 1999, now U.S. Pat. No. 6,545,034.

The invention was made with Government support under Grant No. GM23200 awarded by the National Institute of Health. The Government has certain rights in the invention.

BACKGROUND OF THE INVENTION

Chronic lymphocytic leukemia (CLL) is the most common leukemia in the United States. CLL involves the cancerous proliferation of lymphocytes. It is most common among older adults; 90 percent of the cases are in people more than 50 years old. It occurs 1–3 times more often among men than among women. The onset of CLL tends to be insidious, with symptoms developing gradually. Because it involves an overproduction of mature, functional lymphocytes, persons with this disorder may survive for years. In contrast, in some, the disorder proceeds very rapidly, and requires immediate treatment. Currently, the adenine deoxynucleosides fludarabine (fludara) and 2-chlorodeoxyadenosine (2CdA) are the drugs of choice to treat the disease. However, clinical remissions are seldom induced, and patients eventually succumb from their leukemia.

The number of nonsteroidal anti-inflammatory drugs (NSAIDs) has increased to the point where they warrant separate classification. In addition to aspirin, the NSAIDs available in the U.S. include meclofenamate sodium, oxyphenbutazone, phenylbutazone, indomethacin, piroxicam, sulindac and tolmetin for the treatment of arthritis; mefenamic acid and zomepirac for analgesia; and ibuprofen, fenoprofen and naproxen for both analgesia and arthritis. Ibuprofen, mefenamic acid and naproxen are used also for the management of dysmenorrhea.

The clinical usefulness of NSAIDs is restricted by a number of adverse effects. Phenylbutazone has been implicated in hepatic necrosis and granulomatous hepatitis; and sulindac, indomethacin, ibuprofen and naproxen with hepatitis and cholestatic hepatitis. Transient increases in serum aminotransferases, especially alanine aminotransferase, have been reported. All of these drugs, including aspirin, inhibit cyclooxygenase, that in turn inhibits synthesis of prostaglandins, which help regulate glomerular filtration and renal sodium and water excretion. Thus, the NSAIDs can cause fluid retention and decrease sodium excretion, followed by hyperkalemia, oliguria and anuria. Moreover, all of these drugs can cause peptic ulceration. See, *Remington's Pharmaceutical Sciences*, Mack Pub. Co., Easton, Pa. (18th ed., 1990) at pages 1115–1122.

There is a large amount of literature on the effect of NSAIDs on cancer, particularly colon cancer. For example, see H. A. Weiss et al., *Scand J. Gastroent.*, 31, 137 (1996) (suppl. 220) and Shiff et al., *Exp. Cell Res.*, 222, 179 (1996). More recently, B. Bellosillo et al., *Blood,* 92, 1406 (1998) reported that aspirin and salicylate reduced the viability of B-cell CLL cells in vitro, but that indomethacin, ketoralac and NS-398, did not.

C. P. Duffy et al., *Eur. J. Cancer,* 34, 1250 (1998), reported that the cytotoxicity of certain chemotherapeutic drugs was enhanced when they were combined with certain nonsteroidal anti-inflammatory agents. The effects observed against human lung cancer cells and human leukemia cells were highly specific and not predictable; i.e., some combinations of NSAID and agent were effective and some were not. The only conclusion drawn was that the effect was not due to the cyclooxygenase inhibitory activity of the NSAID.

The Duffy group filed a PCT application (WO98/18490) on Oct. 24, 1997, directed to a combination of a "substrate for MRP", which can be an anti-cancer drug, and a NSAID that increases the potency of the anti-cancer drug. NSAIDs recited by the claims are acemetacin, indomethacin, sulindac, sulindac sulfide, sulindac sulfone, tolmetin and zomepirac. Naproxen and piroxicam were reported to be inactive.

Therefore, a continuing need exists for methods to control cancers, such as leukemias, and to increase the potency of anti-cancer drugs with relatively non-toxic agents.

SUMMARY OF THE INVENTION

In one aspect, the present invention provides a therapeutic method to treat leukemia, e.g. chronic lymphocytic leukemia, comprising administering to a mammal afflicted with leukemia an amount of etodolac, R(−) etodolac, or an analog thereof, effective to inhibit the viability of leukemic cells of said mammal. The present invention also provides a method of increasing the susceptibility of human leukemia cells, such as chronic lymphocytic leukemia (CLL) cells, to a chemotherapeutic agent comprising contacting the cells with an effective sensitizing amount of etodolac, or an analog thereof. Thus, the invention provides a therapeutic method for the treatment of a human or other mammal afflicted with a leukemia such as CLL, wherein an effective amount of etodolac or an analog thereof is administered to a subject afflicted with leukemia and undergoing treatment with a chemotherapeutic ("antineoplastic") agent.

Preferably, the R(−) isomer of etodolac is administered in conjunction with one or more chemotherapeutic agents effective against CLL such as fludarabine (fludara) or 2-chlorodeoxyadenosine (2CdA). Unexpectedly, the R(−) isomer of etodolac, which exhibits little anti-inflammatory activity, was found to be responsible for the sensitizing activity of racemic etodolac. Therefore, the present invention also provides a method to treat other forms of cancer, such as breast, prostate and colon cancer with RS or the R(−) enantiomer of etodolac or an analog thereof, used alone, or preferably, in combination with a chemotherapeutic agent.

A method of evaluating the ability of etodolac to sensitize leukemia cells, such as CLL cells, to a chemotherapeutic agent is also provided. The assay method comprises (a) isolating a first portion of leukemia cells, such as leukemic B cells, from the blood of a human leukemia patient; (b) measuring their viability; (c) administering etodolac, or an analog thereof, to said patient; (d) isolating a second portion of leukemia cells from said patient; (e) measuring the viability of the second portion of leukemia cells; and (f) comparing the viability measured in step (e) with the viability measured in step (b); wherein reduced viability in step (e) indicates that the cells have been sensitized to said chemotherapeutic agent.

Preferably, steps (b) and (e) are carried out in the presence of the chemotherapeutic agent, as will be the case when the leukemia cells are derived from the blood of a mammal afflicted with leukemia, such as a CLL patient.

Thus, a cancer patient about to undergo, or undergoing, treatment for leukemia can be rapidly evaluated to see if he/she will benefit from concurrent chemotherapy and administration of etodolac or an analog thereof.

The present invention is based on the discovery by the inventors that racemic etodolac inhibits the viability of purified CLL cells at concentrations that do not inhibit the viability of normal peripheral blood lymphocytes (PBLs). It was then unexpectedly found that the R(−) enantiomer of etodolac is as toxic to CLL cells as is the S(+) enantiomer. It was then found that etodolac synergistically interacted with fludarabine and 2-chloroadenosine to kill CLL cells at concentration at which the chemotherapeutic agents alone were inactive.

Etodolac and its analogs possess several unique disposition features due to their stereoselective pharmacokinetics. In plasma, after the administration of RS-etodolac, the concentrations of the "inactive" R-enantiomer of etodolac are about 10-fold higher than those of the active S-enantiomer, an observation that is novel among the chiral NSAIDs. See, D. R. Brocks et al., Clin. Pharmacokinet., 26, 259 (1994). After a 200 mg dose in six elderly patients, the maximum plasma concentration of the R-enantiomer was about 33 μM. In contrast, the maximum concentration of the S-enantiomer was 5-fold lower. The typical dosage of the racemic mixture of etodolac is 400 mg BID, and the drug has an elimination half-life between 6–8 hours. Thus, etodolac at commonly used dosages should achieve a plasma concentration of the R-enantiomer shown to sensitize CLL cells in vitro to fludarabine. Moreover, it is likely that the administration of the purified R-enantiomer will not display the side effects associated with cyclooxygenase (COX) inhibitors, such as ulcers and renal insufficiency, and thus could be given at considerably higher dosages. It is believed that etodolac can act both directly and indirectly against cancer cells; i.e., by inhibiting factor(s) that would normally block apoptosis.

DETAILED DESCRIPTION OF THE INVENTION

Figure 1:
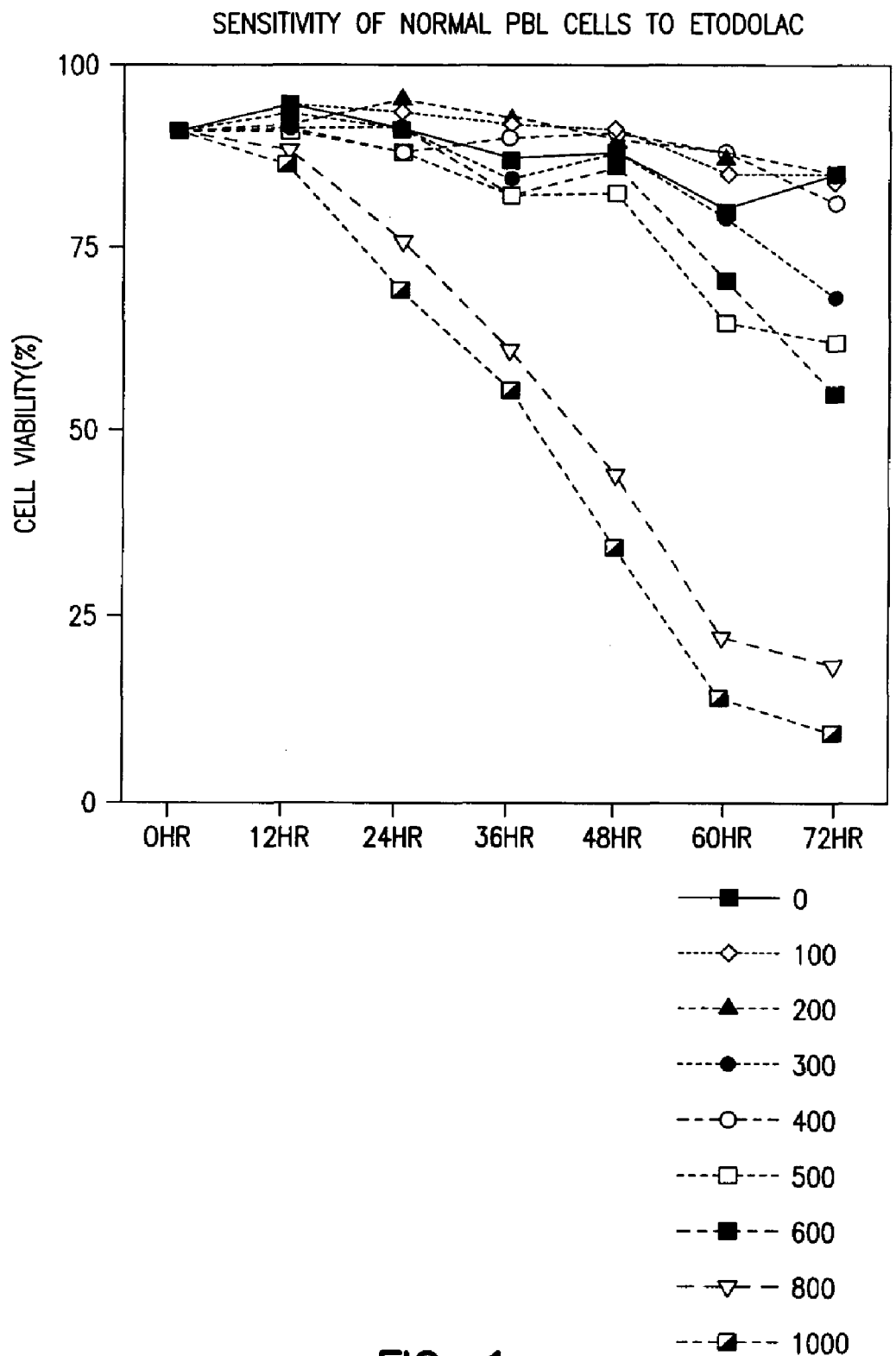
FIG. 1 is a graph depicting the sensitivity of normal peripheral blood lymphocytes (PBL) to racemic etodolac.

Etodolac (1,8-diethyl-1,3,4,9-tetrahydro[3,4-6]indole-1-acetic acid) is a NSAID of the pyranocarboxylic acid class, that was developed in the early 1970s. See, C. A. Demerson et al., Ger. Pat. No. 2,226,340 (Am. Home Products); R. R. Martel et al., Can. J. Pharmacol., 54, 245 (1976). Its structure is formula (I), below: wherein (*) denotes the chiral center. See also, The Merck Index, (11th ed.), at page 608.

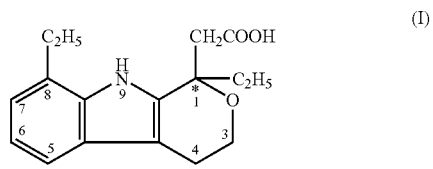

Early studies indicated that etodolac was an effective NSAID, with a favorable ratio of anti-inflammatory activity to adverse effects. Etodolac has been marketed for some years in Europe, including the UK, Italy, France and Switzerland, for the treatment of pain and inflammation associated with various forms of arthritis. The drug was more recently given approval for marketing in the U.S., where its approved uses are currently restricted to the treatment of osteoarthritis, and as a general purpose analgesic.

The pharmacokinetics of etodolac have been extensively reviewed by D. R. Brocks et al., Clin. Pharmacokinet., 26, 259 (1994). Etodolac is marketed as the racemate. However, Demerson et al., J. Med. Chem., 26, 1778 (1983) found that the (+)-enantiomer of etodolac possessed almost all of the anti-inflammatory activity of the racemate, as measured by reduction in paw volume of rats with adjuvant polyarthritis, and prostaglandin synthetase inhibitory activity of the drug. No activity was discernible with the (−)-enantiomer. The absolute configurations of the enantiomers were found to be S-(+) and R-(−), which is similar to that for most other NSAIDs. The enantiomer of the racemate can be resolved by fractional crystallization using optically active 1-phenylethylamine, and use of HPLC to determine racemic etodolac and enantiomeric ratios of etodolac and two hydroxylated metabolites has been reported by U. Becker-Scharfenkamp et al., J. Chromatog., 621, 199 (1993) and B. M. Adger et al. (U.S. Pat. No. 5,811,558). The in vivo disposition of etodolac is extremely stereoselective, with plasma concentrations of the "inactive" R-enantiomer greatly exceeding those of the "active" S-enantiomer. In this respect, etodolac is unique in relation to other chiral NSAIDs, for which the "active" S-enantiomer usually attains plasma concentrations that are similar to or higher than those of the "inactive" enantiomer. Nonetheless, the R(−) enantiomer has been asserted to have some analgesic activity. See, Young et al., U.S. Pat. No. 5,561,151. However, as exemplified below, this unusual disposition facilitates administration of amounts of etodolac that are effective to sensitize leukemic cells to chemotherapeutic agents, without giving rise to the side effects of the "active" anti-inflammatory S(+) enantiomer.

The chemical synthesis of the racemic mixture of etodolac can be performed by the method described in Demerson et al., U.S. Pat. No. 3,843,681; and C. A. Demerson et al., J. Med. Chem., 19(3), 391 (1976), the disclosures of which are hereby incorporated by reference.

The R(−) isomer of etodolac may be obtained by resolution of the mixture of enantiomers of etodolac using conventional means, such as the formation of a diastereomeric salt with a basic optically active resolving acid; see, for example, "Stereochemistry of Carbon Compounds," by E. L. Eliel (McGraw Hill, 1962); C. H. Lochmuller et al., J Chromatog., 113, 283 (1975); "Enantiomers, Racemates and Resolutions," by J. Jacques, A. Collet, and S. H. Wilen, (Wiley-Interscience, New York, 1981); and S. H. Wilen, A. Collet, and J. Jacques, Tetrahedron, 33, 2725 (1977).

Analogs of etodolac that can be used in the present inventions are disclosed inter alia, in C. A. Demerson (U.S. Pat. No. 3,843,681), as compounds of formula (II):

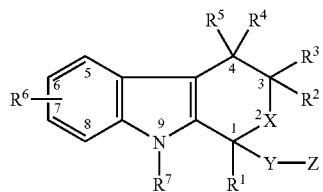

in which $R^1$ is selected from the group consisting of lower alkyl, lower alkenyl, lower alkynyl, lower cycloalkyl, phenyl, benzyl and 2-thienyl, $R^2$, $R^3$, $R^4$ and $R^5$ are the same or different and are each selected from the group consisting of hydrogen and lower alkyl, $R^6$ is selected from the group consisting of hydrogen, lower alkyl, hydroxy, lower alkoxy, benzyloxy, lower alkanoyloxy, nitro and halo, $R^7$ is selected from the group consisting of hydrogen, lower alkyl and lower alkenyl, X is selected from the group consisting of oxy and thio, Y is selected from the group consisting of carbonyl or $(C_1-C_3)$alkylC(O), wherein each alkyl is substituted with 0–2 $(C_1-C_4)$alkyl and Z is selected from the group consisting of hydroxy, lower alkoxy, amino, lower alkylamino, di(lower)alkylamino and phenylamino, or a pharmaceutically acceptable salt thereof. Lower (alkyl, alkenyl, alkanoyl, etc.) indicates a $C_1-C_6$ group, preferably a $C_1-C_4$ group.

The magnitude of a prophylactic or therapeutic dose of racemic or R-etodolac in the acute or chronic management of cancer, i.e., CLL, will vary with the stage of the cancer, such as the solid tumor or leukemia to be treated, the chemotherapeutic agent(s) or other anti-cancer therapy used, and the route of administration. The dose, and perhaps the dose frequency, will also vary according to the age, body weight, and response of the individual patient. In general, the total daily dose range for racemic or R-etodolac, for the conditions described herein, is from about 50 mg to about 5000 mg, in single or divided doses. Preferably, a daily dose range should be about 100 mg to about 2500 mg, in single or divided doses. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective amount" or "an effective sensitizing amount" are encompassed by the above-described dosage amounts and dose frequency schedule.

Any suitable route of administration may be employed for providing the patient with an effective dosage of etodolac, i.e., R(−)etodolac. For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. The etodolac may be administered prior to, concurrently with, or after administration of chemotherapy, or continuously, i.e., in daily doses, during all or part of, a chemotherapy regimen. The etodolac, in some cases, may be combined with the same carrier or vehicle used to deliver the anti-cancer chemotherapeutic agent.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrated agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The invention will be further described by reference to the following detailed examples.

EXAMPLE 1

Sensitivity of Normal Peripheral Blood Lymphocytes and CLL Cells to Etodolac

Mononuclear cells were isolated from the peripheral blood of B-CLL patients and normal donors using density gradient centrifugation (Ficoll-Paque). Cells were cultured at $2\times10^6$ cells per mL in RPMI with 20% autologous plasma in 96-well plates with or without the indicated μM concentrations of etodolac (racemic, S-etodolac, R-etodolac) and in combination with 2-chloro-2'-deoxyadenosine (2CdA) or fludarabine. At indicated times (12, 24, 36, 48, 60, 72 hours), viability assays were performed using the erythrocin B exclusion assay, as described by D. Carson et al., *PNAS USA*, 89, 2970 (1992).

As shown in FIG. 1, significant death of normal PBLs occurred only at 800 μM racemic etodolac, a concentration which cannot be obtained in vivo.

Figure 2:
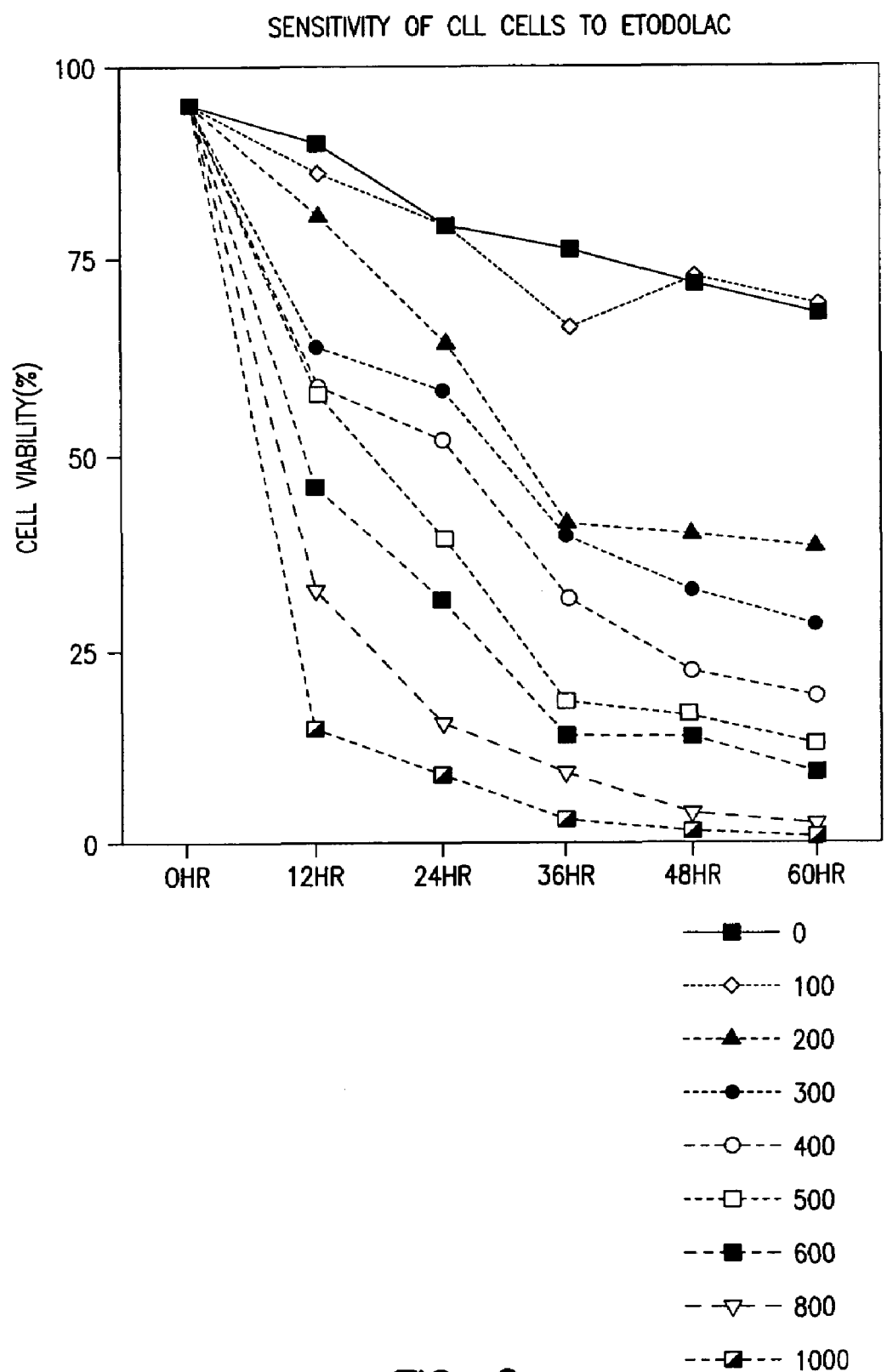
FIG. 2 is a graph depicting the sensitivity of CLL cells to racemic etodolac.

Peripheral blood lymphocytes from a normal donor were cultured with 1.0 mM etodolac for 24 hours. Then B lymphocytes were identified by staining with anti-CD19 antibody, and viability was assessed by $DiOC_6$ fluorescence. Etodolac under these conditions did not reduce the viability of the normal B cells, compared to control cultures. When the same viability assay was run with purified CLL cells from the peripheral blood of a CLL patient, the results were different. As shown in FIG. 2, 50% of the CLL cells were killed by a 48 hour exposure to 200 μM racemic etodolac. More than 95% of the treated cells were malignant B lymphocytes.

EXAMPLE 2

Synergistic Combinations of Etodolac and Chemotherapeutic Agents

Figure 3:
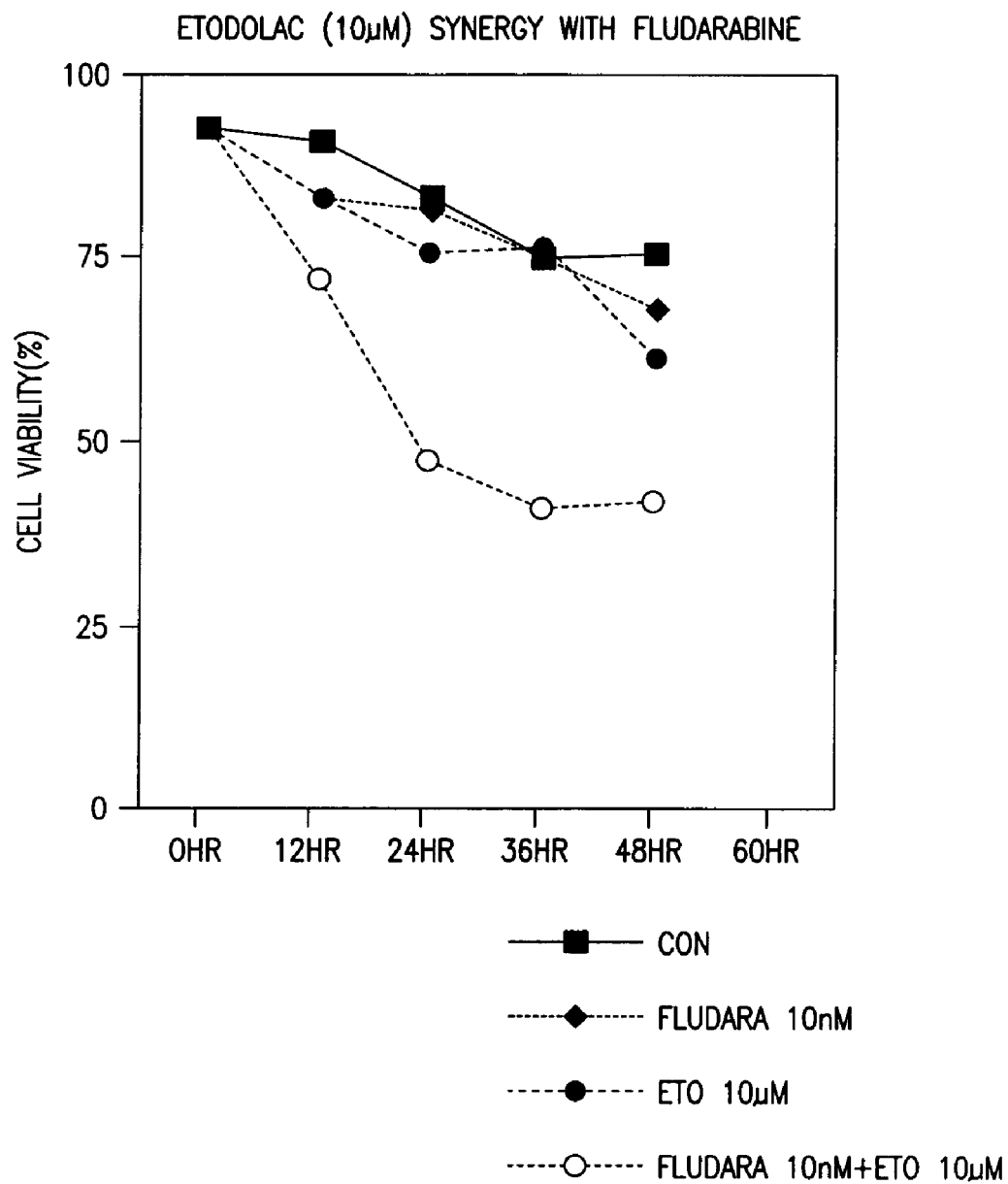
FIG. 3 is a graph depicting the synergistic effect of a combination of racemic etodolac and fludarabine against CLL cells.
Figure 4:
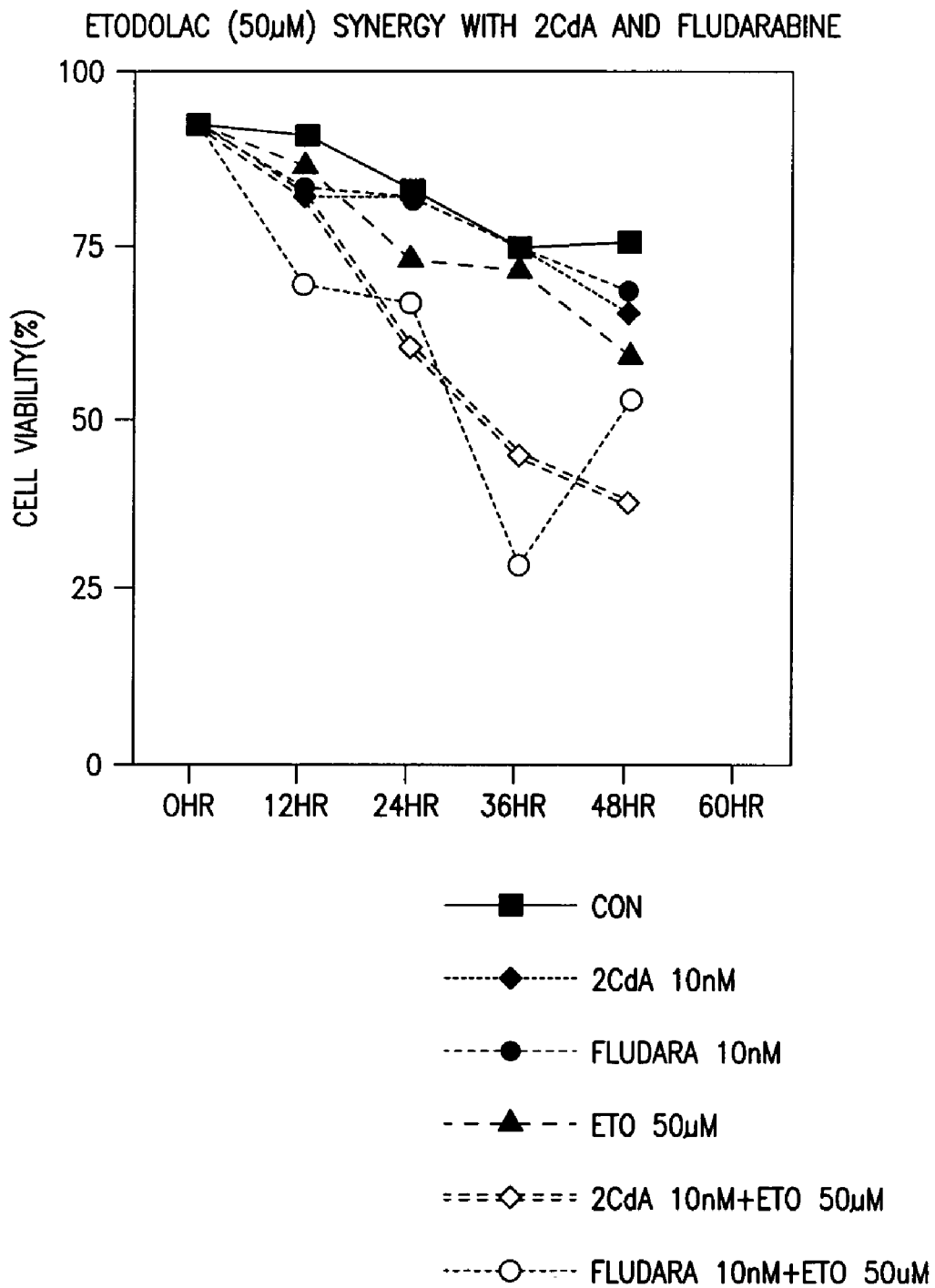
FIG. 4 is a graph depicting the synergistic effect of a combination of 50 μM etodolac with 10 μM 2CdA or 10 mM Fludara against CLL cells.

Fludarabine is a nucleoside analog commonly used for the treatment of CLL. In this experiment the in vitro survival of CLL cells at the indicated time points was compared in cultures containing medium alone ("Con", squares), fludarabine 10 nM (diamonds), etodolac 10 μM (closed circles), and fludarabine 10 nM plus etodolac 10 μM (open circles). The two drugs together exhibited a synergistic cytotoxic effect. FIG. 3 shows that the combination killed 50% of CLL cells during 48 hours of culture, while either drug alone was ineffective. FIG. 4 demonstrates synergy between 50 μM etodolac and 10 nM 2-chlorodeoxyadenosine and fludarabine, under the same test conditions.

EXAMPLE 3

Effect of R(−) and S(+) Etodolac Against CLL Cells

Etodolac tablets were ground in a mortar and extracted from the formulation using ethyl acetate. The resulting racemic mixture of enantiomers was separated into R and S isomers on a preparative scale by fractional crystallization by the procedure of Becker-Scharfenkamp and Blaschke, *J. Chromatog.*, 621, 199 (1993). Thus, the racemic mixture solid was dissolved in absolute 2-propanol and S-1-phenylethylamine was added to the solution. The resulting salt solution was stored in the refrigerator for 4 days. The crystalline white salt product was filtered and washed with cold 2-propanol and recrystallized two more times from 2-propanol. The same procedure was repeated for the R isomer only using R-1-phenylethylamine as the resolving agent. Finally, the R and S salts were decomposed using 10% sulfuric acid (v/v) and extracted with ethyl acetate. The chiral purity of each isomer was verified by HPLC using a Chiral-AGP column from ChromTech.

Figure 5:
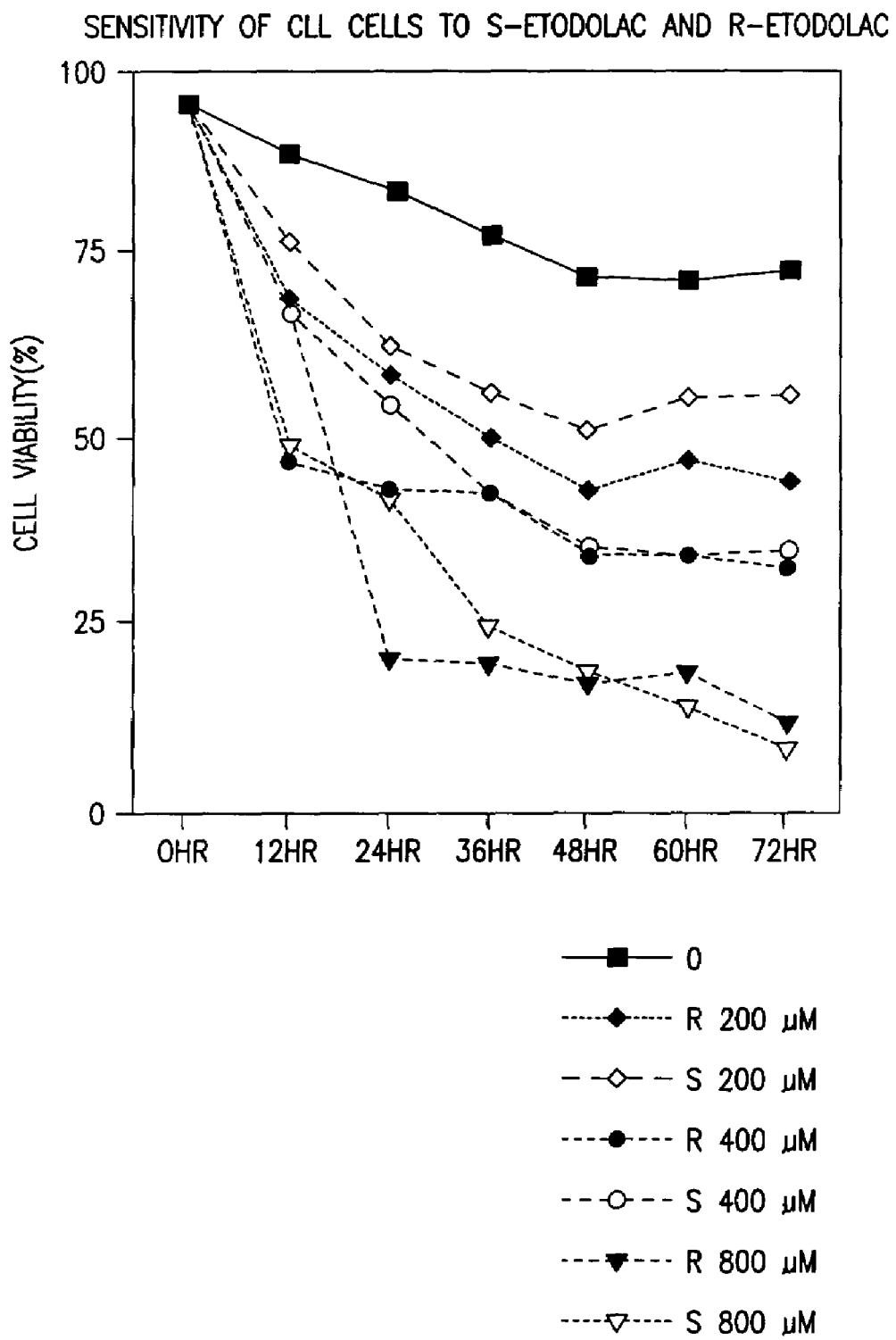
FIG. 5 is a graph depicting the sensitivity of CLL cells to S- and R-etodolac.

The toxicities of the two enantiomers to CLL cells cultured in RPMI 1640 medium with 10% autologous plasma were compared at the indicated concentrations and time points, as shown in FIG. 5. The R- and S-enantiomers are equivalently cytotoxic to the CLL cells.

EXAMPLE 4

Viability of CLL Cells Before and After Etodolac Treatment

Figure 6:
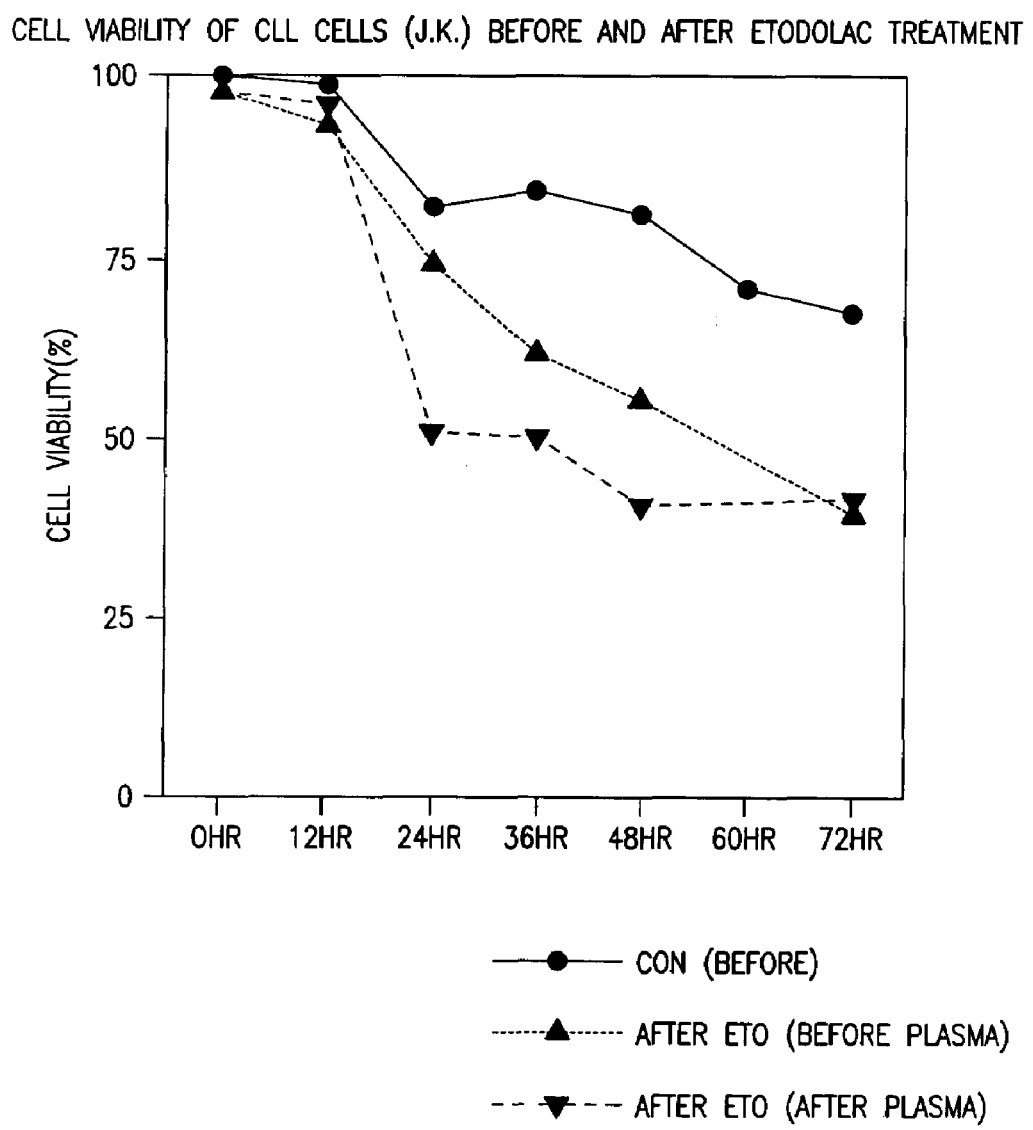
FIGS. 6 and 7 depict the viability of CLL cells from two patients before and after etodolac administration.
Figure 7:
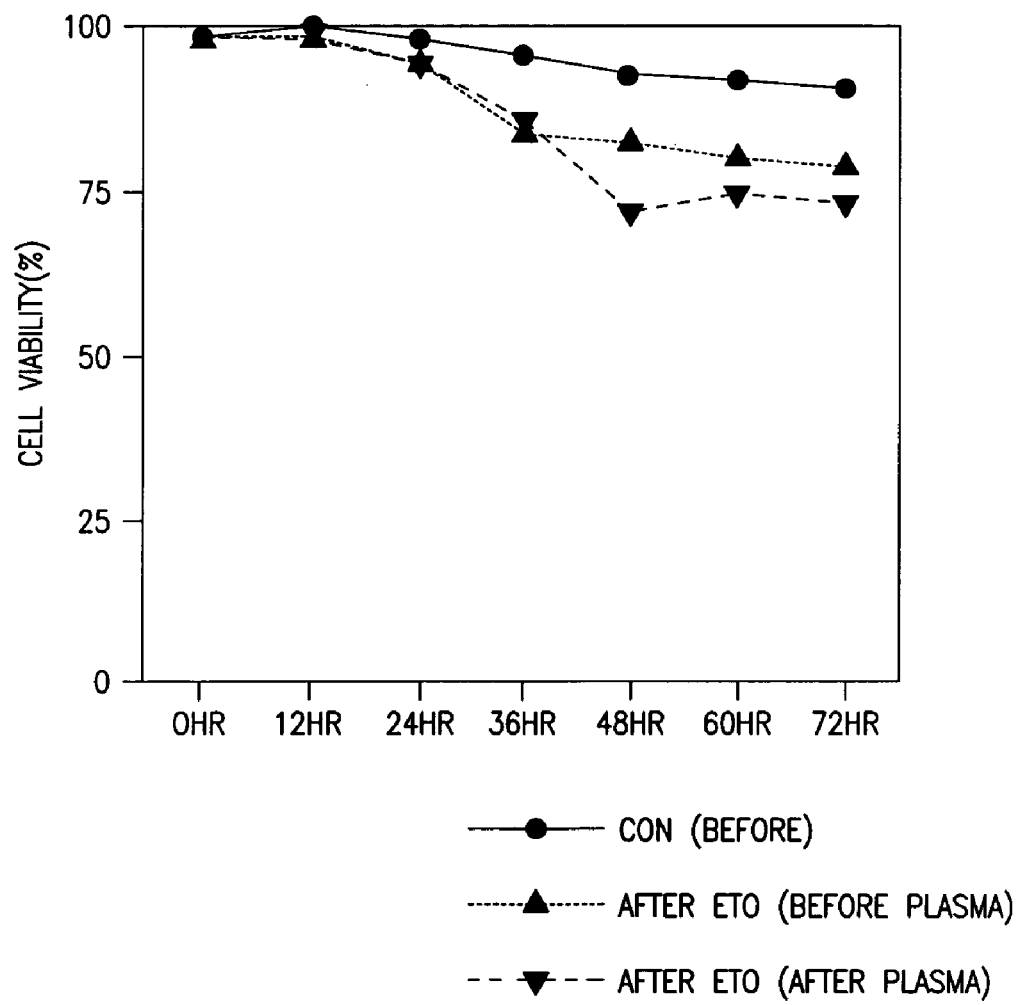
Figure 8A:
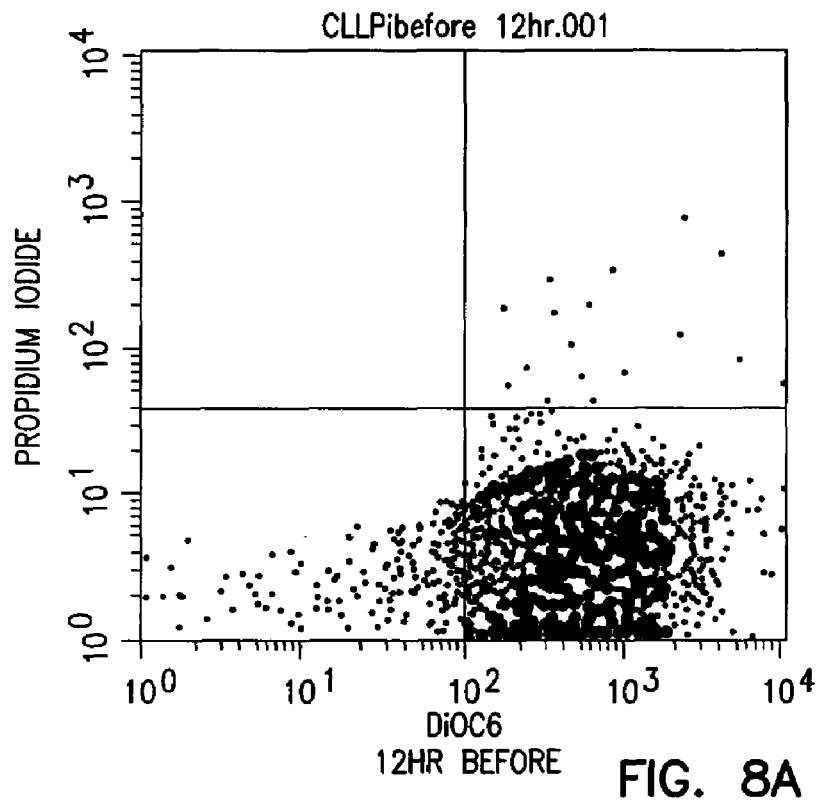
FIGS. 8A, 8B, 8C, and 8D depict a flow cytometric analysis of CLL cells before and after etodolac treatment.
Figure 8B:
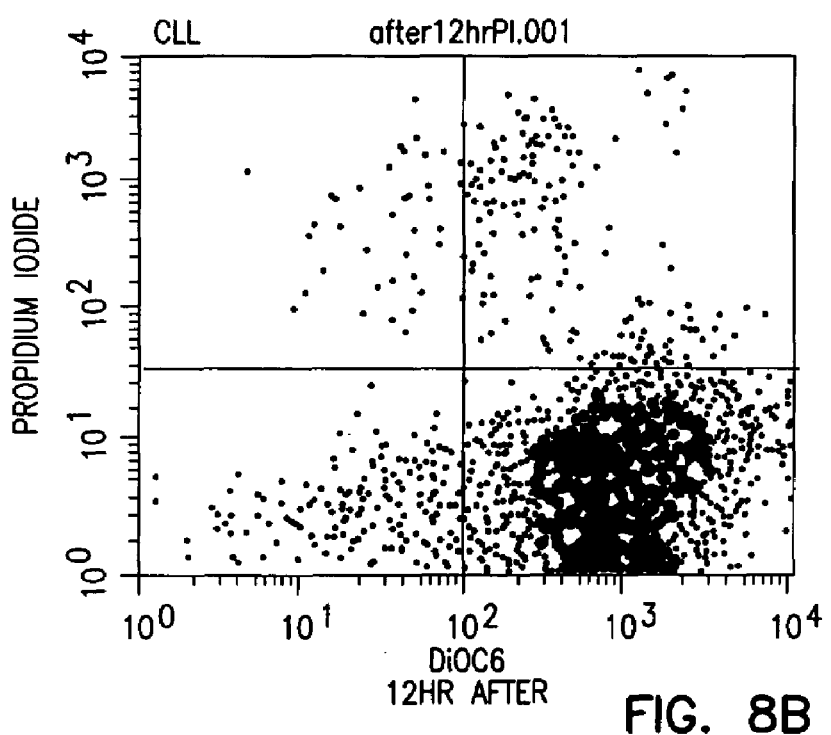
Figure 8C:
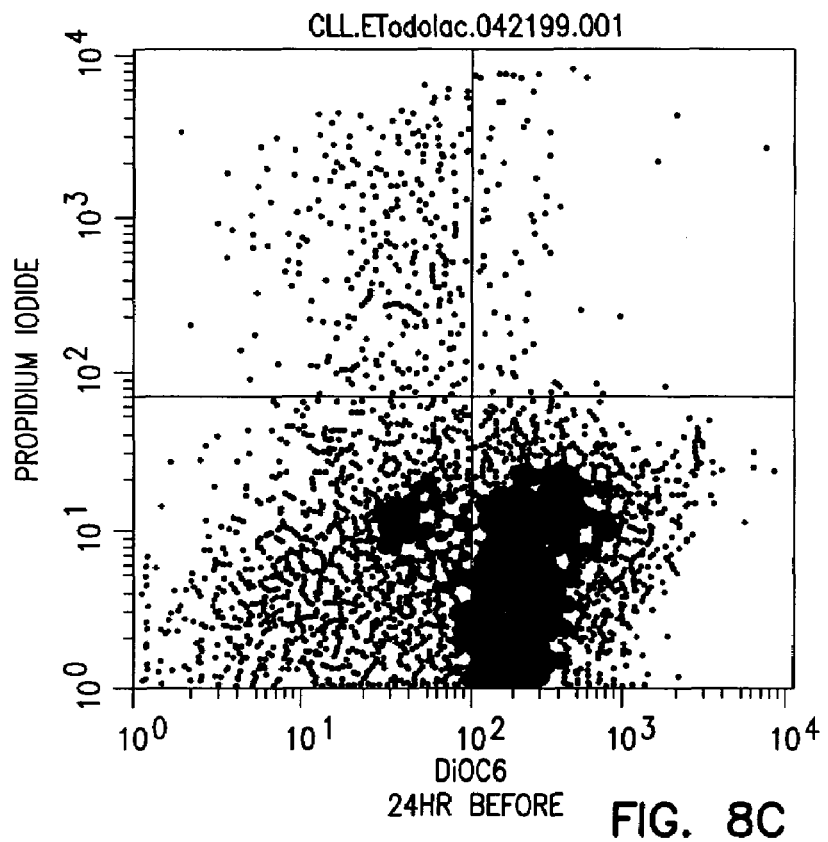
Figure 8D:
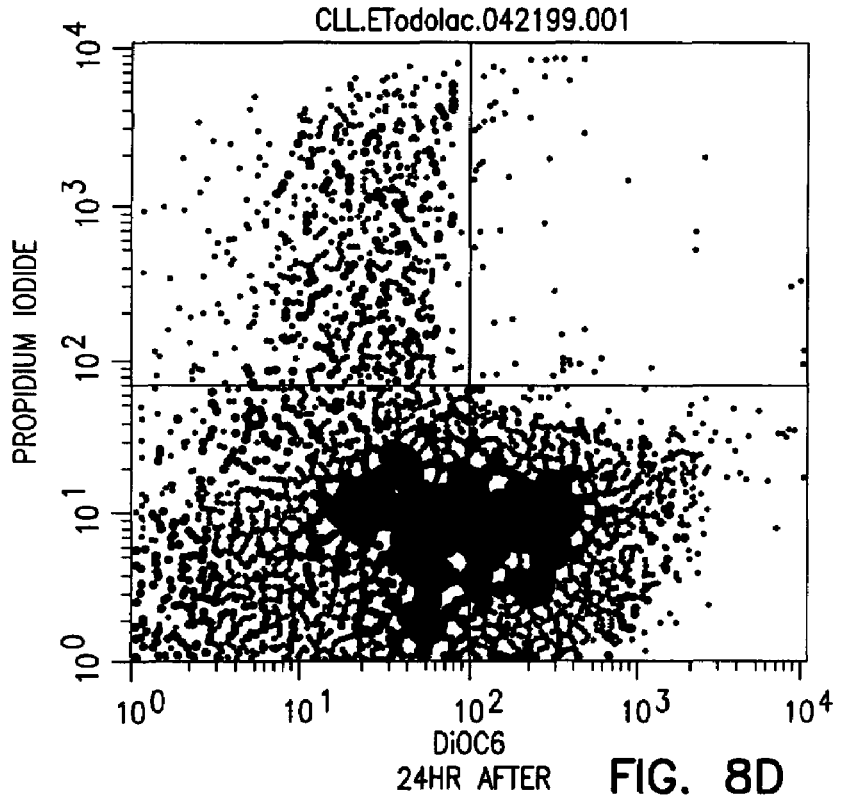

Heparanized blood was taken from two patients (JK and NA) with CLL. Then each patient immediately took a 400 mg etodolac tablet, and a second tablet 12 hours later. After another 12 hours, a second blood specimen was obtained. The CLL cells were isolated and their survival in vitro were compared in RPMI 1640 medium containing 10% autologous plasma, as described in Example 1. The circles show CLL cells before etodolac treatment. In FIGS. 6–7, the upward pointing triangles represent CLL cell viability after etodolac treatment, wherein the cells are dispersed in medium containing the pretreatment plasma. The downward pointing triangles are CLL cells after treatment maintained in medium with the post-treatment plasma.

FIG. 6 shows the different survivals of the two cell populations from patient JK. Note that the cells after treatment had a shortened survival compared to the cells before treatment. FIG. 7 shows a less dramatic but similar effect with patient NA. FIG. 8 is a flow cytometric analysis of CLL cells from patient JK before and after etodolac treatment. $DiOC_6$ is a dye that is captured by mitochondria. When cells die by apoptosis, the intensity of staining decreases. The X axis on the four panels in FIG. 8 shows the $DiOC_6$ staining. An increased number of dots in the left lower box indicates cell death by apoptosis. If one compares the cells taken from the patient before etodolac treatment, and after etodolac treatment, one can see that the number of dots in the left lower box is much higher after the drug. This effect is detectable at 12 hours, and increases further after 24 hours.

To conduct the flow cytometric analysis, the mitochondrial transmembrane potential was analyzed by 3,3' dihexyloxacarboncyanide iodide ($DiOC_6$), cell membrane permeability by propidium iodide (PI)[3] and mitochondrial respiration by dihydrorhodamine 123 (DHR) (See J. A. Royall et al., *Arch. Biochem. Biophys.*, 302, 348 (1993)). After CLL cells were cultured for 12 or 24 hours with the indicated amount of etodolac, the cells were incubated for 10 minutes at 37° C. in culture medium containing 40 nM of $DiOC_6$ and 5 μg/ml PI. Cells were also cultured for 3 hours with the indicated amount of etodolac, spun down at 200×g for 10 minutes and resuspended in fresh respiration buffer (250 mM sucrose, 1 g/L bovine serum albumin, 10 mM $MgCl_2$, 10 mM K/Hepes, 5 mM $KH_2PO_4$ (pH 7.4)) and cultured for 10 minutes at 37° C. with 0.04% digitonin. Then cells were loaded for 5 minutes with 0.1 μM dihydrorhodamine (DHR). Cells were analyzed within 30 minutes in a Becton Dickinson FAC-Scalibur cytofluorometer. After suitable comprehension, fluorescence was recorded at different wavelength: $DiOC_6$ and DHR at 525 nm (Fl-1) and PI at 600 nm (FL-3).

As a general matter a reduction of 10% in the survival of the post-treatment malignant cells, compared to the pretreatment malignant cells, at 16 hours after culture in vitro is considered a "positive" in this test, and indicates the use of etodolac, i.e., R(−) etodolac in CLL or other cancer therapy.

All of the publications and patent documents cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A method of treating prostate cancer in a mammal comprising contacting prostate cancer cells in said mammal with a compound of formula (II):

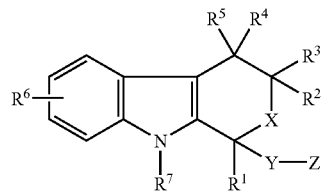

wherein $R^1$ is lower alkyl, lower alkenyl, lower alkynyl, lower cycloalkyl, phenyl or benzyl, $R^2$, $R^3$, $R^4$ and $R^5$ are the same or different and are each hydrogen or lower alkyl; $R^6$ is hydrogen, lower alkyl, hydroxy, lower alkoxy, benzyloxy, lower alkanoyloxy, nitro or halo, $R^7$ is hydrogen, lower alkyl or lower alkenyl; X is oxy; Y is carbonyl or $(C_1-C_3)$alkyl (CO), wherein each alkyl is substituted with 0–2 $(C_1-C_4)$ alkyl, and Z is hydroxy, lower alkoxy, amino, lower alkylamino, di(lower)alkylamino or phenylamino, or a pharmaceutically acceptable salt thereof, wherein the compound of formula (II) is administered in an amount effective to kill prostate cancer cells and to achieve a blood plasma concentration of said compound in the mammal of 200 μM to 600 μM.

2. The method of claim 1 wherein the prostate cancer cells are human cancer cells.

3. The method of claim 2 wherein the compound of formula (II) is etodolac.

4. The method of claim 3 wherein the etodolac is R(−) etodolac.

5. The method of claim 2 wherein the compound of formula (II) is administered orally.

6. The method of claim 1 wherein said amount is effective to achieve a concentration of the compound of formula (II) in blood plasma of 300 μM to 600 μM.

7. The method of claim 6 wherein said amount is effective to achieve a concentration of the compound of formula (II) in blood plasma of 300 μM to 500 μM.

8. The method of claim 7 wherein said amount is effective to achieve a concentration of the compound of formula (II) in blood plasma of 400 μM to 500 μM.

* * * * *